United States Patent
Rodan et al.

(10) Patent No.: US 6,296,840 B1
(45) Date of Patent: Oct. 2, 2001

(54) MASQUE

(75) Inventors: Kathryn P. Rodan, Piedmont; Kathy A. Fields, San Francisco, both of CA (US); Kenneth Klein, Fairlawn; David Garlen, Summit, both of NJ (US)

(73) Assignee: Rodan & Fields, LLC, Oakland, CA (US)

( * ) Notice: Subject to any disclaimer, the term of this patent is extended or adjusted under 35 U.S.C. 154(b) by 0 days.

(21) Appl. No.: 09/631,366

(22) Filed: Aug. 2, 2000

Related U.S. Application Data

(60) Provisional application No. 60/147,578, filed on Aug. 6, 1999.

(51) Int. Cl.$^7$ .................................................. A61K 7/021
(52) U.S. Cl. ............................ 424/63; 424/400; 424/401; 424/78.03
(58) Field of Search ................................... 424/69, 78.03, 424/401, 402, 443; 514/844, 846, 859, 937, 944

(56) References Cited

U.S. PATENT DOCUMENTS

| | | | | |
|---|---|---|---|---|
| 4,014,995 | * | 3/1977 | Juliano et al. | 424/168 |
| 4,965,071 | * | 10/1990 | Kawan | 424/401 |
| 5,618,850 | * | 4/1997 | Coury et al. | 514/772.2 |
| 5,955,062 | * | 9/1999 | McEleney et al. | 424/59 |

* cited by examiner

Primary Examiner—James M. Spear
Assistant Examiner—Charesse L. Evans
(74) Attorney, Agent, or Firm—Thomas R. Lampe

(57) ABSTRACT

A colored facial masque is formed from a paste which is produced by mixing a dry powder masque component. The dry powder masque component includes a first water soluble colorant and said liquid masque component includes a second water soluble colorant, the colors of said first and second water soluble colorants differing from the color of the facial masque.

14 Claims, No Drawings

MASQUE

This application is based on and claims the benefit of U.S. Provisional Patent Application No. 60/147,578, filed Aug. 6, 1999.

TECHNICAL FIELD

This invention relates to a facial masque.

BACKGROUND OF THE INVENTION

It has been known that Algin can be cross linked with divalent or trivalent metal salts to form a rubbery masque that sets up in four to five minutes.

DISCLOSURE OF INVENTION

According to the teachings of this invention a therapeutic agent is added to a masque as a means to deliver medication to the skin. A further object of this invention is to provide an unexpected and surprising color reaction when the masque is prepared. The masque also heats upon application to thermally treat the face before cooling of the masque in situ.

BEST MODE FOR CARRYING OUT THE INVENTION

The masque consists of two parts, part 1 being a powder product prepared in accordance with the formulation indicated below in which a water soluble food colorant is added in a quantity low enough so the color cannot be seen in the white powder yet high enough to interact with the color present in part 2, the activator for the masque.

Part 2 liquid activator is prepared in accordance with the formulation indicated below and also contains a water soluble food colorant present in a concentration sufficient to brightly color the clear liquid. In practice two ounces of activator liquid are mixed with a ½ ounce of powder to form a paste. Immediately upon mixing, the hidden color in the powder mixing with the color in the liquid changes the color of the masque. This paste is applied to the skin and allowed to sit approximately four minutes after which it forms a rubbery masque, which can be lifted from the skin surface. The therapeutic object is accomplished by allowing the active ingredient to remain in contact with the skin during the period in which the masque is hardening and for the masque to absorb and remove excess oils from the skin surface. The masque heats and then subsequently cools.

Any number of unique color effects can be achieved by selected appropriate colors in the powder and activator. For example, a yellow color hidden in the powder combined with blue color in the activator produces a green masque. Red color in the powder combined with blue in the activator provides a purple masque. Other unexpected colors of masques can be achieved by selection of desired colors in the individual parts.

Representative Part 1 and Part 2 formulations indicating the purposes of each ingredient are as follows:

MASQUE DRY POWDER (PART 1)

| No. | Phase | Ingredient | % by Weight | Purpose |
|---|---|---|---|---|
| 1 | A | ALGIN | 15.63 | GELLANT |
| 2 | A | MAGNESIUM CARBONATE | 58.41 | FILLER |
| 3 | A | CALCIUM SULFATE | 15.66 | CROSS LINKING AGENT |
| 4 | A | TETRASODIUM PYROPHOSPHATE | 6.70 | ALKALINE SOURCE |
| 5 | A | FRAGRANCE | 0.30 | FRAGRANCE |
| 6 | A | IMIDAZOLIDINYL UREA | 0.30 | PRESERVATIVE |
| 7 | A | SULFUR | 2.00 | ANTI-ACNE AGENT |
| 8 | A | WATER SOLUBLE FOOD COLOR 1% PREMILLED IN MAGNESIUM CARBONATE | 1.00 | HIDDEN COLOR |
| Total: | | | 100.00 | |

Manufacturing instructions: Combine and micropulverize. Add 2 oz. of Activator Soln. to ½ oz. of Powder. Mix well for one minute and apply to face with spatula. It will set into a peelable elastic masque in 4 min.

MASQUE LIQUID ACTIVATOR (PART 2)

| No. | Phase | Ingredient | % by Weight | Purpose |
|---|---|---|---|---|
| 1 | A | WATER | 95.70 | SOLVENT |
| 2 | A | GLYCERYL POLY-METHYL-METHACRYLATE | 1.50 | PLASTISIZER |
| 3 | A | PROPYLENE GLYCOL | 2.00 | SOLUBLEIZER |
| 4 | A | DIAZOLININYL UREA | 0.30 | PRESERVATIVE |
| 5 | A | METHYL PARABEN | 0.17 | PRESERVATIVE |
| 6 | B | PROPYL PARABEN | 0.03 | PRESERVATIVE |
| 7 | C | WATER SOLUBLE FOOD COLOR (1% Soln.) | 0.30 | VISIBLE COLOR |

Manufacturing Instructions: Combine Phase A. Combine Phase B. Add Phases B and C to Phase A. Mix to clarity.

Formulations within the scope of this invention can include other ingredients or medications. For example, salacyclic acid, Retinol, Vitamin C or other anti-oxidants can be employed to treat signs of aging. Moisturizing agents for treatment of dry skin can be utilized in the masque composition, examples being sesame oil and squalene. Hydroquinone or other bleaching agents can be added to fade brown spots.

We claim:

1. A method of preparing a facial masque and employing the facial mask for skin care treatment, said method comprising the steps of:
   preparing a dry powder masque component including a first water soluble colorant;
   preparing a liquid masque component including a second water soluble colorant;
   incorporating at least one therapeutic agent into at least one of the masque components;
   mixing said dry powder masque component and said liquid masque component to form a masque paste incorporating said at least one therapeutic agent to be applied to a person's face;
   during said mixing step, combining said first water soluble colorant and said second water soluble colorant to create a masque paste color differing from the color of said first water soluble colorant and the color of said second water soluble colorant;
   applying the masque paste to the person's face to form a masque having substantially the same color as said masque paste and which differs from the color of said first water soluble colorant and the color of said second water soluble colorant;
   leaving the masque paste on the person's face a sufficient period of time to harden the masque and to allow the masque to provide skin care treatment; and
   removing the masque from the person's face.

2. The method according to claim 1 wherein said step of preparing a dry powder masque component includes limiting the quantity of said first water soluble colorant in said dry powder masque component so that the color of said first water soluble colorant is not readily visually perceptible.

3. The method according to claim 1 wherein said step of preparing a liquid masque component includes introducing a quantity of said second water soluble colorant in said liquid masque component sufficient to cause the liquid masque component to assume the color of said second water soluble colorant.

4. A colored facial masque for application to a user's face to provide skin care treatment and for subsequent removal from the user's face, said masque being formed from a masque paste produced by mixing a dry powder masque component with a liquid masque component, at least one of said masque components incorporating at least one therapeutic agent, said dry powder masque component including a first water soluble colorant and said liquid masque component including a second water soluble colorant, said first water soluble colorant and said second water soluble colorant operable to form the color of said facial masque when mixed, said first and second water soluble colorants prior to mixing having colors differing from the color of said masque paste and said facial masque and said masque hardening on the person's face during skin care treatment and prior to removal from the person's face.

5. The method according to claim 1 including the step of generating heat from said paste.

6. The colored facial masque according to claim 4 including a moisturizing agent.

7. The colored facial masque according to claim 4 including a bleaching agent for fading brown spots.

8. The colored facial masque according to claim 4 wherein the colors of said first and second water soluble colorants differ from one another.

9. The colored facial masque according to claim 4 wherein the first water soluble colorant is not readily visually perceptible in said dry powder masque component.

10. The colored facial masque according to claim 4 wherein the liquid masque component is the color of said second water soluble colorant.

11. The colored facial masque according to claim 4 wherein at least one of said first water soluble colorant and said second water soluble colorant is a food colorant.

12. The colored facial masque according to claim 4 including a heat generating component for heating the masque.

13. The colored facial masque according to claim 4 wherein said therapeutic agent is an anti-oxidant.

14. The colored facial masque according to claim 4 wherein said therapeutic agent is an anti-acne agent.

* * * * *